(12) United States Patent
Lee et al.

(10) Patent No.: US 9,393,201 B2
(45) Date of Patent: Jul. 19, 2016

(54) OXALIPLATIN NANOPARTICLES AND METHOD FOR PREPARING SAME

(75) Inventors: Sung Jae Lee, Bucheon-si (KR); Young Hoon Kim, Seoul (KR); Sang Heon Lee, Daejeon (KR); Kab Sig Kim, Seoul (KR)

(73) Assignees: JW Pharmaceutical Corporation, Seoul (KR); Bio-Synectics, Inc., Seoul (KR)

( * ) Notice: Subject to any disclaimer, the term of this patent is extended or adjusted under 35 U.S.C. 154(b) by 1005 days.

(21) Appl. No.: 13/497,208

(22) PCT Filed: Sep. 20, 2010

(86) PCT No.: PCT/KR2010/006459
§ 371 (c)(1),
(2), (4) Date: Mar. 20, 2012

(87) PCT Pub. No.: WO2011/034394
PCT Pub. Date: Mar. 24, 2011

(65) Prior Publication Data
US 2012/0177728 A1     Jul. 12, 2012

(30) Foreign Application Priority Data
Sep. 21, 2009   (KR) .......................... 10-2009-0089079

(51) Int. Cl.
| | |
|---|---|
| *A61K 9/50* | (2006.01) |
| *A61K 9/14* | (2006.01) |
| *A61K 31/555* | (2006.01) |
| *A61K 9/00* | (2006.01) |
| *A61K 9/10* | (2006.01) |
| *A61K 47/38* | (2006.01) |
| *A61K 9/20* | (2006.01) |
| *A61K 9/48* | (2006.01) |

(52) U.S. Cl.
CPC .............. *A61K 9/146* (2013.01); *A61K 9/0095* (2013.01); *A61K 9/10* (2013.01); *A61K 9/2027* (2013.01); *A61K 9/4866* (2013.01); *A61K 31/555* (2013.01); *A61K 47/38* (2013.01); *Y10T 428/2982* (2015.01)

(58) Field of Classification Search
CPC ........... A61K 9/14; A61K 9/141; A61K 9/51; B01D 1/28; B01D 1/2881; C08F 6/14; C08F 6/22

USPC ................................. 424/464–489, 490–502
See application file for complete search history.

(56) References Cited

U.S. PATENT DOCUMENTS

| | | | |
|---|---|---|---|
| 5,716,988 A | 2/1998 | Ibrahim et al. | |
| 6,287,593 B2 | 9/2001 | Cherian | |
| 6,306,902 B1 | 10/2001 | Anderson et al. | |
| 6,476,068 B1 | 11/2002 | Lauria et al. | |
| 7,217,735 B1 | 5/2007 | Au et al. | |
| 2003/0109515 A1 | 6/2003 | Lauria et al. | |
| 2004/0127557 A1 | 7/2004 | Ibrahim et al. | |
| 2005/0142205 A1* | 6/2005 | Rashba-Step | A61K 9/0019 424/490 |
| 2009/0053302 A1 | 2/2009 | Boulikas | |
| 2010/0166872 A1* | 7/2010 | Singh | A61K 9/5138 424/499 |

FOREIGN PATENT DOCUMENTS

| | | |
|---|---|---|
| KR | 367752 | 12/2002 |
| KR | 2005-00054819 | 6/2005 |
| KR | 2007-0067768 | 6/2007 |
| KR | 2007-0107841 | 11/2007 |
| KR | 913063 | 8/2009 |
| WO | WO 2005/020980 A | 3/2005 |

OTHER PUBLICATIONS

Lui, Wei et al.: "Preparation of oxaliplatin phospholipid complex and its nanosuspension", *Journal of Shenyang Pharmaceutical University*, vol. 24, No. 4, Apr. 2007, pp. 197-200, in Chinese but English Translation of Abstract Appears on p. 200.

* cited by examiner

*Primary Examiner* — Micah-Paul Young
(74) *Attorney, Agent, or Firm* — Frommer Lawrence & Haug LLP (57) ABSTRACT

The present invention relates to a nanoparticle of oxaliplatin, which is a water-soluble active substance, a pharmaceutical composition containing the same, and a method for preparing an orally administrable oxaliplatin nanoparticle by 5 emulsifying a lipid mixture solution wherein a solid lipid and a surfactant are mixed in an aqueous mixture solution wherein oxaliplatin and a specific cosolvent are mixed and then removing the solid lipid and the cosolvent using a supercritical fluid gas.

6 Claims, 6 Drawing Sheets

OXALIPLATIN NANOPARTICLES AND METHOD FOR PREPARING SAME

This application is a 371 of PCT/KR2010/006459 filed on Sep. 20, 2010, published on Mar. 24, 2011, under publication number WO 2011/034394 A which claims priority benefits to Korean Patent Application Number 10-2009-0089079 filed Sep. 21, 2009, the disclosure of which is incorporated herein by reference.

TECHNICAL FIELD

The present invention relates to a nanoparticle of oxaliplatin, which is a water-soluble active substance, a pharmaceutical composition containing the same, and a method for preparing an orally administrable oxaliplatin nanoparticle by emulsifying a lipid mixture solution wherein a solid lipid and a surfactant are mixed in an aqueous mixture solution wherein oxaliplatin and a specific cosolvent are mixed and then removing the solid lipid and the cosolvent using a supercritical fluid gas.

BACKGROUND ART

Oncology is a branch of medicine that deals with cancer patients mainly parenterally (intravenously) rather than with oral drugs. During the past decade, there has been an increase in the treatment using parenteral drugs while little progress has been made in the oral drug therapy. Currently, more than 20 cytotoxic oral anticancer drugs are known. Most of the developed oral drugs were developed from previously known parenteral ones.

Some of the oral anticancer drugs were approved recently and others are studied consistently. The oral drug therapy is advantageous in terms of convenience and easiness of administration. With the acceleration in the development of oral drugs, the oral drug therapy is also expected to develop fast as well.

For taxane-based anticancer drugs, there has been an attempt to administer the P-glycoprotein inhibitor together in order to improve bioavailability for oral administration and many studies are under way in order to allow for oral administration of taxane drugs.

5-Fluorouracil (5-FU), which is commonly used in the treatment of gastrointestinal cancers including stomach cancer, is not suitable for oral administration because of low bioavailability and is known to induce side effects such as diarrhea. Capecitabine is an orally-administered chemotherapeutic agent. It is a prodrug that is enzymatically converted to 5-fluorouracil in the tumor. Capecitabine exhibits toxicity comparable to that of intravenously-administered 5-fluorouracil and is approved globally for use in breast cancer and colon cancer and is a successful case of oral anticancer drug development (V J O'Neil and C J Twelves, *British Journal of Cancer* (2002) 87: 933-937).

Among platinum-based anticancer drugs including oxaliplatin, satraplatin is the first and only orally-administered platinum-based chemotherapeutic drug.

Thousands of platinum complex derivatives have been synthesized and tested in preclinical phases, but only about 30 of them have entered into the clinical phase (Lloyd R Kelland, *Expert Opinion on Investigational Drugs* (2000) 9(6): 1373-1382). Currently, only 3 of them, i.e., cisplatin, carboplatin and oxaliplatin, are approved by the USFDA and are used in the form of injection (Hak Choy et al., *Clin. Cancer Res.* (2008) 14(6): 1633-1638).

Oxaliplatin is an organic complex consisting of platinum and 1,2-diaminocyclohexane and having an oxalate ligand as a leaving group. Its IUPAC name is (R,R)-1,2-diaminocyclohexane(ethanedioato-O,O)platinum. Currently, oxaliplatin is marketed for treatment of advanced colorectal cancer and metastatic stomach cancer under the brand name Eloxatin®. Frequently, it is administered together with 5-fluorouracil or leucovorin.

Metastatic colon cancer is treated by chemotherapy using Eloxatin® (oxaliplatin), FOLFOX (fluorouracil/leucovorin/oxaliplatin) or FOLFIRI (fluorouracil/leucovorin), and Genentech/Roche's Avastin® (bevacizumb) was approved in 2004 by the USFDA.

Oxaliplatin is administered only as injection and Eloxatin®, which is in a lyophilized form, needs to be diluted with water for Injection or glucose solution before its administration to a patient. The lyophilization process is complicated, costly and requires reconstitution. During the reconstitution, problems such as loss of oxaliplatin, precipitation, formation of undesirable particles, pollution, etc. may occur. Especially, the problem of pollution is of great importance when considering the toxicity of the antitumor substance.

Liquid formulation for injection is marketed recently in order to improve the inconvenience and problem of the lyophilized oxaliplatin for injection, but attempt to prepare oxaliplatin into orally-administrable form is not known yet.

Although satraplatin was first developed as orally-administered platinum-based drug and reported in 1993, it has not yet received approval from the USFDA for treatment of prostate cancer (In-Sung Park, Recent Trends in KOTRA (2007)).

Although the reason why oxaliplatin can be used only in the form of injection was not reported in detail, it was revealed from clinical tests that cisplatin and carboplatin, which are both platinum(II) complexes like oxaliplatin, exhibit very low bioavailability in the gastrointestinal tract when administered orally (Lloyd R Kelland, *Expert Opinion on Investigational Drugs* (2000) 9(6): 1373-1382).

Satraplatin is a platinum(IV)-based oral drug developed to solve the low bioavailability of the platinum(II) compound. Recently, the result of clinical trial phase III was reported for the compound (Hak Choy et al., *Clin. Cancer Res.* (2008) 14(6): 1633-1638).

Although the necessity of the development of orally-administrable anticancer drugs and their many advantages over injections are well understood, a number of restrictions including low bioavailability slow development thereof.

As for oxaliplatin, attempts have been made to prepare a stable aqueous solution of oxaliplatin to improve the aforesaid problems. U.S. Pat. No. 5,716,988 discloses a preparation of oxaliplatin for parenteral administration comprising an aqueous solution of oxaliplatin, in a concentration of 1-5 mg/mL, and with a pH in the range of 4.5-6. And, U.S. Pat. Nos. 6,476,068 and 6,306,902 disclose a pharmaceutically stable solution formulation comprising oxaliplatin and a method for preparing the same. Korean Patent No. 367,752 discloses a stably lyophilized pharmaceutical composition, Korean Patent No. 913,063 discloses a readily-usable injection solution containing oxaliplatin, and International Patent No. WO/2005/020980 discloses an oxaliplatin formulation for parenteral administration. In addition, US Patent Application Publication Nos. 2003-0109515 and 2004-0127557 disclose methods for preparing more stable composition, and Korean Patent Application Publication No. 10-2007-0067768 discloses a method for preparing a stable oxaliplatin composition with minimized toxicity of oxaliplatin.

Meanwhile, U.S. Pat. No. 7,217,735 discloses a pharmaceutical composition for oral administration comprising nanoparticles of hardly soluble paclitaxel. However, since the solvents described in the specification cannot dissolve water-soluble active substances such as oxaliplatin, the patent is inapplicable to preparation of nanoparticles of the water-soluble active substances.

At present, nanotechnology is used to dissolve drugs which have good physiological activities but are hardly soluble in aqueous solutions. Also, the technology allows for improvement of bioavailability by enhancing drug stability or maintenance of drug concentration in blood by controlling release rate. The drug stabilization using the nanotechnology contributes to the improvement of bioavailability and maintenance of long-term efficacy of such drugs as paclitaxel, docetaxel, doxorubicin, etc. which have the problems of solubility and stability (KIPO, 2006 Patent Litigation Map Project—Development of Nanopharmaceuticals (2006)).

However, although studies have been made on improved composition types and preparation thereof, nanoparticularization of hardly soluble active substances, or the like for parenteral administration of oxaliplatin, no orally administrable formulation comprising oxaliplatin only has been developed yet.

DISCLOSURE

Technical Problem

The inventors of the present invention have researched to prepare the water-soluble active substances such as oxaliplatin as a formulation for oral administration. As a result, they have found that nanoparticles can be obtained by emulsifying a lipid mixture solution wherein a solid lipid and a surfactant are mixed in an aqueous mixture solution wherein oxaliplatin and a specific cosolvent are mixed and then pressurizing using a supercritical fluid gas and that they can be prepared into a formulation for oral administration.

The present invention is directed to providing oxaliplatin nanoparticles for oral administration with high bioavailability, obtained by emulsifying the lipid mixture solution in the aqueous mixture solution and then removing the solid lipid using the supercritical fluid gas.

Technical Solution

In one general aspect, the present invention provides an oxaliplatin nanoparticle for oral administration having an average particle size of 10-1000 nm and a pharmaceutical composition for oral administration containing the same.

In another general aspect, the present invention provides a method for preparing an oxaliplatin nanoparticle for oral administration, including: (1) dissolving oxaliplatin in a cosolvent which is water, dimethyl sulfoxide (DMSO) or a mixture thereof to obtain an aqueous mixture solution; (2) mixing a solid lipid with a surfactant to obtain a lipid mixture solution; (3) adding the lipid mixture solution to the aqueous mixture solution to obtain an emulsion and then cooling and drying the same to obtain a solid; and (4) adding the solid to a reactor, pressurizing above a supercritical condition by adding a supercritical fluid gas and removing the solid lipid and the cosolvent using the supercritical fluid gas to obtain an oxaliplatin nanoparticle.

Advantageous Effects

By providing oxaliplatin, which is currently available only in injection form for parenteral administration, in the form of a nanoparticle, the present invention allows for the development of orally administrable oxaliplatin which is stable against gastric acid and has improved bioavailability, thereby improving patient compliance through avoiding the inconvenience of injection and greatly reducing medical cost. Since the oxaliplatin nanoparticle can be prepared economically using a relatively inexpensive supercritical fluid producing facility, it can be prepared via a simple process with high yield in commercial scale.

BEST MODE

The present invention relates to an oxaliplatin nanoparticle which is a water-soluble active substance. The nanoparticle is prepared by a method comprising: (1) dissolving oxaliplatin in a cosolvent which is water, dimethyl sulfoxide (DMSO) or a mixture thereof to obtain an aqueous mixture solution; (2) mixing a solid lipid with a surfactant to obtain a lipid mixture solution; (3) adding the lipid mixture solution to the aqueous mixture solution to obtain an emulsion and then cooling and drying the same to obtain a solid; and (4) adding the solid to a reactor, pressurizing above a supercritical condition by adding a supercritical fluid gas and removing the solid lipid and the cosolvent using the supercritical fluid gas to obtain an oxaliplatin nanoparticle.

Hereinafter, each step of the method for preparing the nanoparticle according to the present invention will be described in detail.

First, oxaliplatin, which is a water-soluble active substance, is dissolved in a cosolvent to obtain an aqueous mixture solution. It is because the water-soluble active substance cannot be dissolved sufficiently with the solid lipid used in the present invention. The cosolvent may be water, dimethyl sulfoxide (DMSO) or a mixture thereof. The cosolvent sufficiently dissolves the oxaliplatin because it is highly polar unlike commonly used alcohols, and prevents $CO_2$ gas from remaining in the composition because of high solubility under the supercritical condition.

When dissolving the oxaliplatin in the cosolvent, an anticoagulant may be further added to prevent aggregation of nanoparticles. The anticoagulant may be a monosaccharide, a polysaccharide, a dietary fiber, a gum, a protein, or the like.

More specifically, mannitol, sucrose, lactose, glucose, trehalose, glycerol, fructose, maltose, dextran, polyethylene glycol, glycine, alanine, lysine, etc. may be used. Most specifically, mannitol may be used. The anticoagulant may be used in an amount of 10-100 parts by weight, more specifically 20-60 parts by weight, based on 100 parts by weight of the oxaliplatin.

Then, a solid lipid is mixed with a surfactant to obtain a lipid mixture solution.

The solid lipid may be a lipid which maintains solid phase at room temperature, melts easily upon heating with a relatively low melting point of 30-100° C. such that it can act as a solvent for the active substance and has high solubility for a supercritical fluid. For example, the solid lipid may be selected from a group consisting of a $C_{10}$-$C_{22}$ alcohol, saturated fatty acid and ester thereof, a mono- or diglyceride compound having a $C_{10}$-$C_{22}$ fatty acid group, a $C_{16}$ or higher hydrocarbon and a fatty acid reduced compound of a $C_{10}$-$C_{22}$ triglyceride compound. Specifically, a $C_{10}$-$C_{22}$ alcohol may be used. More specifically, a $C_{12}$-$C_{15}$ alcohol may be used.

The surfactant used in the present invention needs to one capable of preventing aggregation of the oxaliplatin, being dissolved well by the solid lipid, allowing easy control of the size of the nanoparticle so that emulsification occurs well, and not being easily removed by the supercritical fluid. Specifically, gelucire, solutol, poloxamer, or the like may be used. Being highly potent, the surfactant allows for the preparation of small and uniform oxaliplatin nanoparticles.

The oxaliplatin and the surfactant are included at a weight ratio of 1:0.1-2.0, more specifically 1:0.5-1.5. When the amount of the surfactant is less than the aforesaid range, stability of emulsion may be degraded. And, when the amount exceeds the aforesaid range, nanoparticles may not be formed owing to aggregation with the surfactant.

The lipid mixture solution is added to the aqueous mixture solution to obtain an emulsion. Specifically, while slowly adding the lipid mixture solution to obtain an emulsion, heating is performed at 40-100° C., more specifically at 50-80° C., so that the solid lipid may serve as a solvent for the water-soluble active substance. To obtain the oxaliplatin nanoparticle as a small and uniform nanoparticle with size 300 nm or smaller, the emulsification process is of great importance. When the aqueous mixture solution is added to the lipid mixture solution, emulsification does not proceed since phase separation occurs. Thus, the lipid mixture solution should be slowly added to the aqueous mixture solution while heating. Specifically, when the aqueous mixture solution contains 1 g of oxaliplatin, the lipid mixture solution may be added at a rate of 50-100 g/min.

Then, the emulsion is cooled and dried to obtain a solid. When the solidification occurs at room temperature via spontaneous cooling, a nanoparticle cannot be obtained because of increased particle size. Therefore, the emulsion is cooled quickly to 20-30° C. in 10-60 seconds and then dried at the temperature.

The obtained solid is added to a reactor of a supercritical extractor and, after adding a supercritical fluid gas, pressure is increased above the supercritical condition. Specifically, the solid may be pulverized. The pulverization may be performed according to a method known in the art. After the pulverization, the resulting particle has a smaller size and a larger surface area, thus facilitating removal of the solid lipid.

The supercritical fluid gas refers to an inert gas that can become a supercritical fluid under specific temperature and pressure, i.e., under the supercritical temperature and the supercritical pressure, such as carbon dioxide or nitrogen gas.

After the supercritical fluid gas is slowly added to the reactor, pressure is increased above the supercritical condition. The pressure inside the reactor may be controlled between 50 and 200 atm in general, although the pressure is determined according to the size of the reactor and the quantity of the mixture. The temperature inside the reactor is maintained below the melting point of the solid lipid, specifically at 10-40° C. When the reactor temperature inside the reactor is too high, the surfactant melts and, as a consequence, the active substance and the anticoagulant that have been uniformly distributed in the mixture undergo crystal growth. As a result, a uniform nanoparticle cannot be obtained. After the pressure inside the reactor is increased above the pressure where the supercritical fluid gas becomes a supercritical fluid or a subcritical fluid, the reactor may be rotated so that the supercritical fluid or the subcritical fluid can sufficiently penetrate into the solid.

Figure 1:
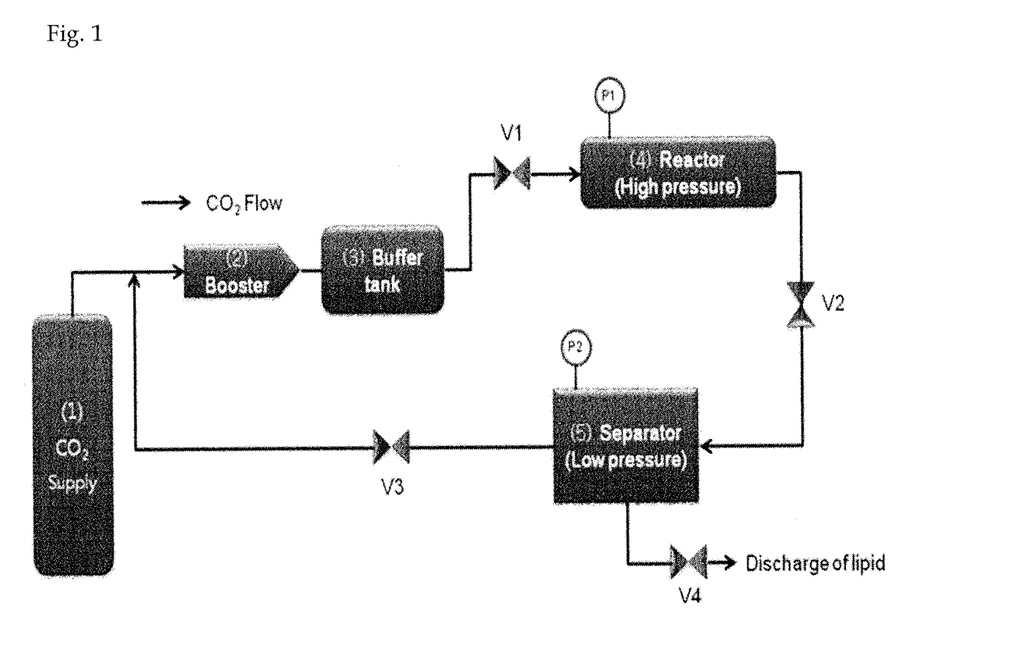
FIG. 1 schematically shows a process for preparing an oxaliplatin nanoparticle using a supercritical fluid gas.

FIG. 1 shows an exemplary process for preparing an oxaliplatin nanoparticle using the supercritical fluid gas. The process is achieved largely in three portions, i.e., a supercritical fluid ($CO_2$) buffer tank (1-3), a reactor (4) and a separator (5). First, the solid is pulverized and added to the reactor. Then, the reactor is rotated while supplying the supercritical fluid to the reactor from the supercritical fluid buffer tank. Subsequently, the supercritical fluid is circulated to remove the solid lipid and the cosolvent while controlling the pressure inside the reactor between 50 and 200 atm. Due to the pressure difference, the solid lipid and the cosolvent are dissolved in the supercritical fluid and collected by the separator, and a mixture of the oxaliplatin nanoparticle and the surfactant remains in the reactor.

The oxaliplatin nanoparticle obtained by the method has a size of 10-1000 nm, specifically 10-500 nm, more specifically 10-300 nm.

Having a zeta potential of −30 to −70 mV when dispersed in a cosolvent, the oxaliplatin nanoparticle can be stabilized without aggregation between particles. Zeta potential is an electric potential outside a particle and is a measure of the electrostatic interaction between individual particles, denoting stability of a dispersion, especially a suspension, in which particles are dispersed. The dispersion can be maintained stably below the zeta potential, since the particles strongly repel each other. However, when the absolute value of the zeta potential is smaller than the aforesaid range, the particles may aggregate owing to van der Waals force because of weak repulsion between the particles.

The present invention further provides a pharmaceutical composition comprising the oxaliplatin nanoparticle.

After the solid lipid and the cosolvent are removed, a composition wherein the oxaliplatin nanoparticle and the surfactant are mixed is obtained. The composition comprises the oxaliplatin nanoparticle and the surfactant at a weight ratio of 1:0.1-2.0, specifically 1:0.5-1.5, without change from the initially added amount.

The pharmaceutical composition may be prepared into a formulation for oral administration by further comprising one or more adjuvant selected from excipient, binder, disintegrant and lubricant. Specifically, it may be prepared into tablet, suspension, capsule, or the like.

The excipient may be selected from lactose, microcrystalline cellulose, low-substituted hydroxypropyl cellulose, corn starch, potato starch, wheat starch, white sugar, D-mannitol, precipitated calcium carbonate, dextrin or pre-gelatinized starch. The binder may be polyvinylpyrrolidone, hydroxypropyl cellulose, dextrin, gelatin, methyl cellulose, hydroxyethyl cellulose, hydroxymethyl cellulose, polyvinyl alcohol, paste or gum arabic. The disintegrant may be sodium starch glycolate, crospovidone, croscarmellose sodium, low-substituted hydroxypropyl cellulose, starch, or calcium carboxymethyl cellulose. The lubricant may be colloidal silicon dioxide, magnesium stearate, talc, anhydrous silicate, or the like.

[MODE FOR INVENTION]

The examples and experiments will now be described. The following examples and experiments are for illustrative purposes only and not intended to limit the scope of the present invention.

Example 1

Oxaliplatin (1 g) was completely dissolved in dimethyl sulfoxide (25 g) at 70° C. to obtain an aqueous mixture solution. Separately from this, poloxamer (0.5 g) was completely dissolved in a solid lipid myristyl alcohol (60 g) for 5 minutes to obtain a lipid mixture solution. The lipid mixture solution was slowly added to the aqueous mixture solution while slowly stirring at 10,000 rpm or above using a homogenizer so that emulsification occurred at 80° C. Thus obtained emulsion was quickly cooled to 25° C. to prepare a solid with the oxaliplatin uniformly distributed in the lipid as fine particles, which was then pulverized using a pulverizer. The pulverized solid was added to a reactor of a supercritical extractor and the reactor was rotated while supplying $CO_2$ gas. The solid lipid myristyl alcohol and the dimethyl sulfoxide were completely removed by circulating $CO_2$ while maintaining the pressure inside the reactor at 70 atm or above. Finally, 1.5 g of a composition comprising an oxaliplatin nanoparticle with an average particle size of 300 nm or smaller was obtained.

Example 2

Oxaliplatin (1 g) was completely dissolved in dimethyl sulfoxide (25 g) at 70° C. to obtain an aqueous mixture solution. Separately from this, solutol (0.2 g) was completely dissolved in a solid lipid myristyl alcohol (60 g) at 70° C. for 5 minutes to obtain a lipid mixture solution. The lipid mixture solution was slowly added to the aqueous mixture solution while slowly stirring at 10,000 rpm or above using a homogenizer so that emulsification occurred at 80° C. Thus obtained emulsion was quickly cooled to 25° C. to prepare a solid with the oxaliplatin uniformly distributed in the lipid as fine particles, which was then pulverized using a pulverizer. The pulverized solid was added to a reactor of a supercritical extractor and the reactor was rotated while supplying $CO_2$ gas. The solid lipid myristyl alcohol and the dimethyl sulfoxide were completely removed by circulating $CO_2$ while maintaining the pressure inside the reactor at 70 atm or above. Finally, 1.2 g of a composition comprising an oxaliplatin nanoparticle with an average particle size of 300 nm or smaller was obtained.

Example 3

Oxaliplatin (1 g) and mannitol (0.4 g) were completely dissolved in purified water (90 g) at 70° C. to obtain an aqueous mixture solution. Separately from this, Gelucire 44/14 (1 g) was completely dissolved in a solid lipid myristyl alcohol (90 g) at 70° C. for 5 minutes to obtain a lipid mixture solution. The lipid mixture solution was slowly added to the aqueous mixture solution while slowly stirring at 10,000 rpm or above using a homogenizer so that emulsification occurred at 80° C. Thus obtained emulsion was quickly cooled to 25° C. to prepare a solid with the oxaliplatin uniformly distributed in the lipid as fine particles, which was then pulverized using a pulverizer. The pulverized solid was added to a reactor of a supercritical extractor and the reactor was rotated while supplying $CO_2$ gas. The solid lipid myristyl alcohol and the purified water were completely removed by circulating $CO_2$ while maintaining the pressure inside the reactor at 70 atm or above. Finally, 2.4 g of a composition comprising an oxaliplatin nanoparticle with an average particle size of 300 nm or smaller was obtained.

Example 4

Oxaliplatin (1 g) and mannitol (0.4 g) were completely dissolved in purified water (90 g) at 70° C. to obtain an aqueous mixture solution. Separately from this, solutol (1 g) was completely dissolved in a solid lipid myristyl alcohol (90 g) at 70° C. to obtain a lipid mixture solution. The lipid mixture solution was slowly added to the aqueous mixture solution while slowly stirring at 10,000 rpm or above using a homogenizer so that emulsification occurred at 80° C. Thus obtained emulsion was quickly cooled to 25° C. to prepare a solid with the oxaliplatin uniformly distributed in the lipid as fine particles, which was then pulverized using a pulverizer. The pulverized solid was added to a reactor of a supercritical extractor and the reactor was rotated while supplying $CO_2$ gas. The solid lipid myristyl alcohol and the purified water were completely removed by circulating $CO_2$ while maintaining the pressure inside the reactor at 70 atm or above. Finally, 2.4 g of a composition comprising an oxaliplatin nanoparticle with an average particle size of 300 nm or smaller was obtained.

Example 5

Oxaliplatin (1 g) and mannitol (0.4 g) were completely dissolved in purified water (90 g) at 70° C. to obtain an aqueous mixture solution. Separately from this, poloxamer (1 g) was completely dissolved in a solid lipid myristyl alcohol (90 g) at 70° C. for 5 minutes to obtain a lipid mixture solution. The lipid mixture solution was slowly added to the aqueous mixture solution while slowly stirring at 10,000 rpm or above using a homogenizer so that emulsification occurred at 80° C. Thus obtained emulsion was quickly cooled to 25° C. to prepare a solid with the oxaliplatin uniformly distributed in the lipid as fine particles, which was then pulverized using a pulverizer. The pulverized solid was added to a reactor of a supercritical extractor and the reactor was rotated while supplying $CO_2$ gas. The solid lipid myristyl alcohol and the purified water were completely removed by circulating $CO_2$ while maintaining the pressure inside the reactor at 70 atm or above. Finally, 2.4 g of a composition comprising an oxaliplatin nanoparticle with an average particle size of 300 nm or smaller was obtained.

Example 6

Oxaliplatin (1 g) was completely dissolved in dimethyl sulfoxide (25 g) at 70° C. to obtain an aqueous mixture solution. Separately from this, poloxamer (3.0 g) was completely dissolved in a solid lipid myristyl alcohol (90 g) for 5 minutes to obtain a lipid mixture solution. The lipid mixture solution was slowly added to the aqueous mixture solution while slowly stirring at 10,000 rpm or above using a homogenizer so that emulsification occurred at 80° C. Thus obtained emulsion was quickly cooled to 25° C. to prepare a solid with the oxaliplatin uniformly distributed in the lipid as fine particles, which was then pulverized using a pulverizer. The pulverized solid was added to a reactor of a supercritical extractor and the reactor was rotated while supplying $CO_2$ gas. The solid lipid myristyl alcohol and the dimethyl sulfoxide were completely removed by circulating $CO_2$ while maintaining the pressure inside the reactor at 70 atm or above. Finally, 4.0 g of a composition comprising an oxaliplatin nanoparticle was obtained.

Test Example 1

Measurement of Particle Size Distribution and Zeta Potential of Oxaliplatin Nanoparticle The oxaliplatin nanoparticles (5 g) prepared in the foregoing examples were completely dispersed in anhydrous ethanol (10 mL) and particle size distribution was measured using a particle size analyzer (Otsuka, ELS-Z). The result is given in Table 1.

TABLE 1

Particle size distribution (nm) of oxaliplatin nanoparticle

|  | D10 | D50 | D90 |
|---|---|---|---|
| Example 1 | 256 | 290 | 376 |
| Example 2 | 210 | 253 | 394 |
| Example 3 | 145 | 183 | 235 |
| Example 4 | 118 | 179 | 295 |
| Example 5 | 123 | 168 | 260 |

As seen from Table 1, particles with an average particle size of 300 nm or smaller could be obtained. It is to be noted that the prepared nanoparticles had a narrow particle size distribution.

In order to investigate the stability of the oxaliplatin nanoparticle when dispersed in a solvent, zeta potential was measured using ELS-8000 (Otsuka) in colloidal state. The result is given in Table 2.

TABLE 2

|  | Zeta potential (mV) |
|---|---|
| Example 1 | −44.7 |
| Example 2 | −59.3 |
| Example 3 | −51.1 |
| Example 4 | −35.3 |
| Example 5 | −60.9 |

In general, it is known that aggregation or crystallization of particles does not occur when the zeta potential is about −30 mV. Since the oxaliplatin nanoparticle of the present invention exhibits a zeta potential of between about −35 and about −60 mV, it shows very superior electrostatic stability in solution.

Test Example 2

SEM Measurement of Oxaliplatin Nanoparticle

Figure 2:
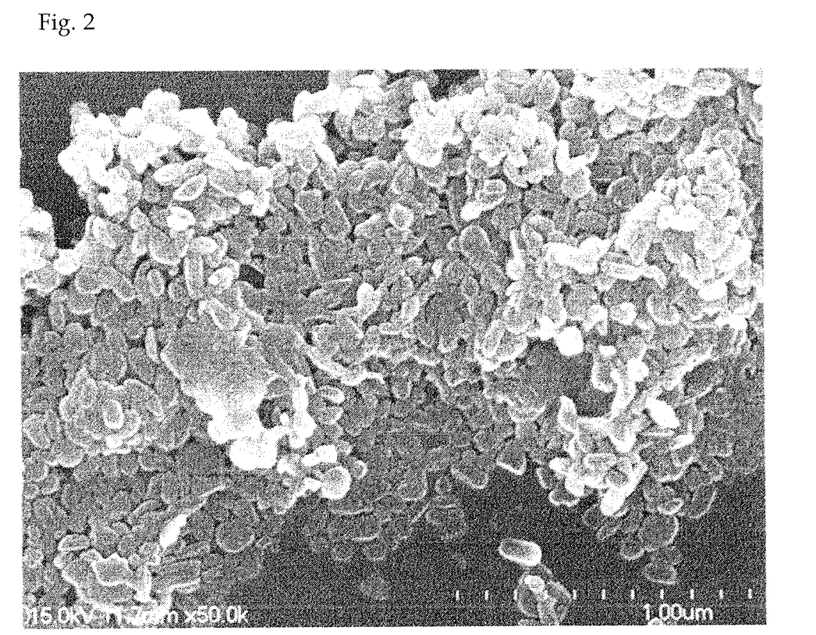
FIG. 2 shows an SEM image of an oxaliplatin nanoparticle prepared in Example 5.
Figure 3:
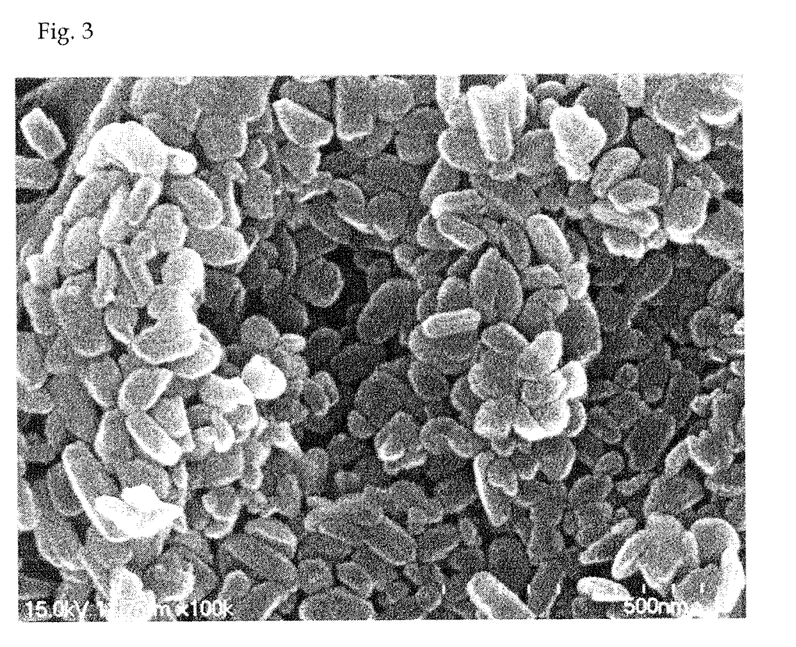
FIG. 3 shows an SEM image of the oxaliplatin nanoparticle prepared in Example 5.
Figure 4:
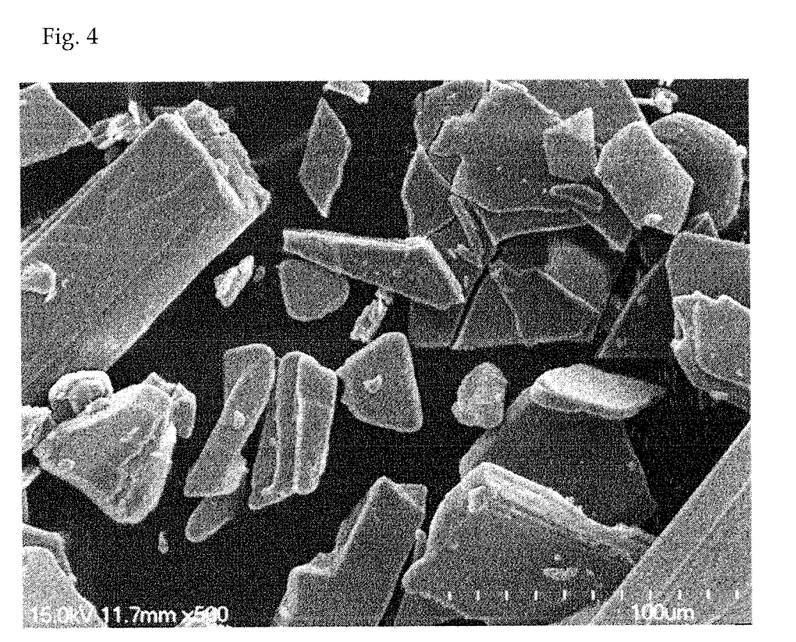
FIG. 4 shows an SEM image of an oxaliplatin powder.

Particle size and shape of the oxaliplatin nanoparticle prepared in Example 5 were observed using a scanning electron microscope (S-4700N, Hitachi). The result is shown in FIGS. 2 and 3. For comparison, an SEM image of oxaliplatin powder used as source material is shown in FIG. 4.

As seen from FIGS. 2 and 3, the oxaliplatin nanoparticle of Example 5 has a uniform nano-scale particle size.

Figure 5:
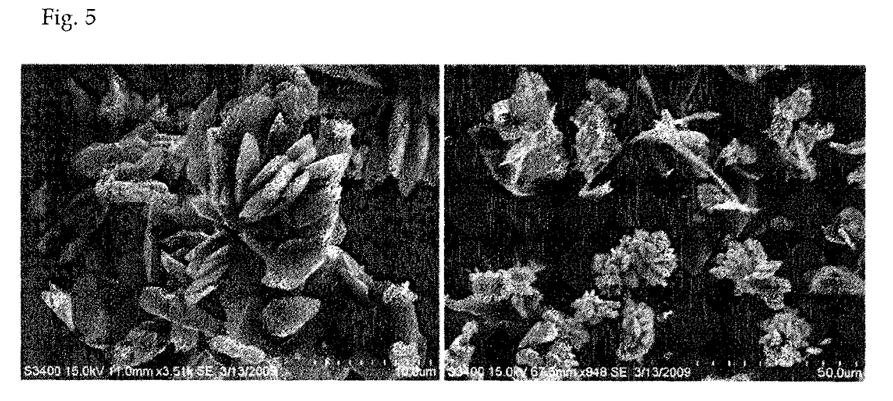
FIG. 5 shows an SEM image of an oxaliplatin nanoparticle prepared in Example 6.

FIG. 5 shows an SEM image of the oxaliplatin particle prepared in Example 6. It can be seen that, owing to the excess surfactant, the nanoparticles aggregated resulting in a particle size larger than 50 μm. Accordingly, it was confirmed that control of the surfactant content is necessary to prepare a stable and uniformly-sized nanoparticle.

Test Example 3

Solubility Measurement of Oxaliplatin Nanoparticle

The oxaliplatin nanoparticle (12 mg) prepared in Example 5 was dispersed in 50 mL of pH 4.0 USP acetate buffer and pH 6.8 phosphate buffer, respectively, at 25° C. Then, after taking 1 mL of sample at different times, followed by centrifugation for 15 minutes at 3500 rpm, HPLC analysis (Agilent 1200 series, Hewlett Packard, USA) was conducted.

HLPC condition:
Capcell Pak C18 column, flow rate 1.1 mL/min, detection wavelength 210 nm
Mobile phase: pH 3.0, phosphoric acid/acetonitrile=99/1 (v/v)

For comparison, concentration was also measured for oxaliplatin powder (5 mg) at different times as described above. The result is shown in FIGS. 6 and 7.

Figure 6:
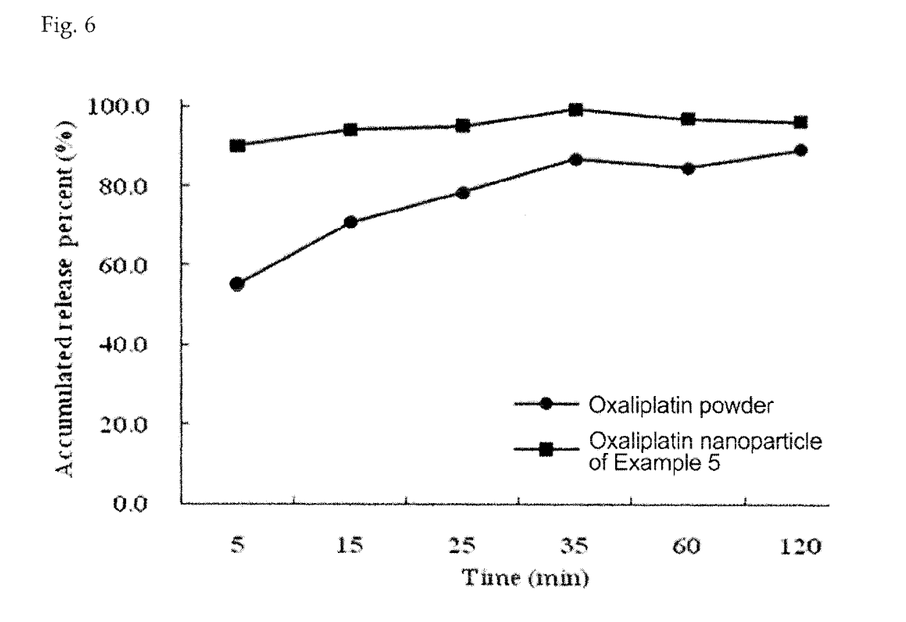
FIG. 6 shows a result of comparing solubility of the oxaliplatin nanoparticle prepared in Example 5 with that of an oxaliplatin powder with time in pH 4.0 USP acetate buffer.
Figure 7:
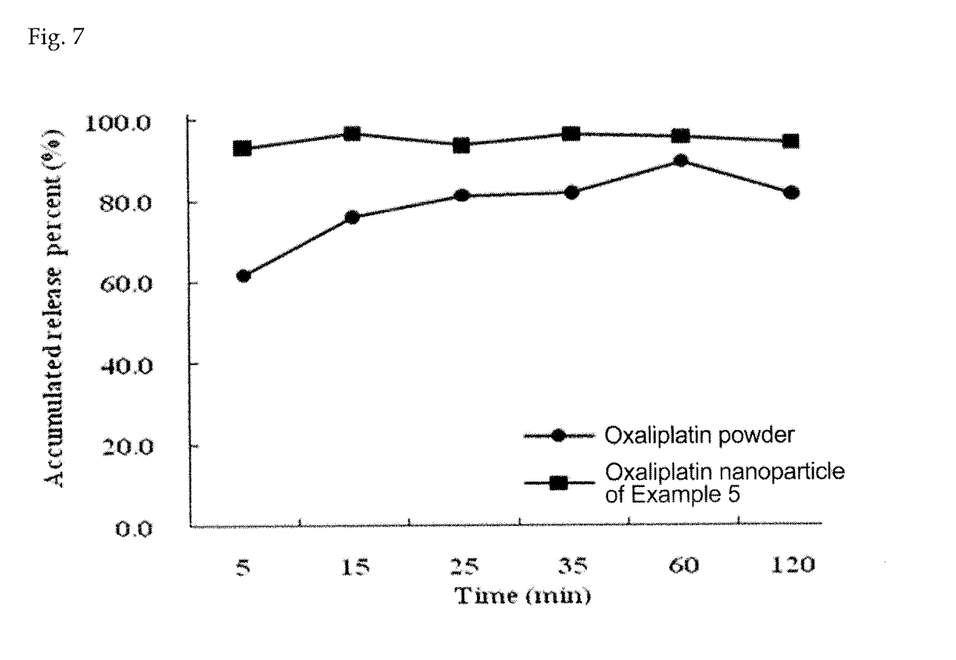
FIG. 7 shows a result of comparing solubility of the oxaliplatin nanoparticle prepared in Example 5 with that of an oxaliplatin powder with time in pH 6.8 phosphate buffer.

As seen from FIGS. 6 and 7, the oxaliplatin nanoparticle the present invention showed a solubility close to 90% in 5 minutes, whereas the oxaliplatin powder exhibited the maximum solubility in 2 hours. The improvement of solubility is achieved owing to the increased surface area of the nanoparticle and allows for easier preparation into formulation for oral administration such as suspension.

Test Example 4

Cell Viability Assay

SW620 and HCT116 cells (ATCC CCL-227, USA) were seeded on a 96-well plate, with $5 \times 10^3$ cells/50 μL per each well. 4 hours later, the cells were treated with the oxaliplatin particle of Example 5 or oxaliplatin powder at 10 mM. After incubation at 37° C. for 72 hours, the cells were treated with 100 μL of CellTiter-Glo (CellTiter-Glo®, Promega, Cat. # G7573) reagent. Then, after lysing the cells in an orbital shaker for 2 minutes, followed by stabilization for 10 minutes, luminescence was measured using a luminometer (Envision, PerkinElmer).

$GI_{50}$ value was calculated from the luminescence measurement result. Anticancer activity of the oxaliplatin powder and the nanoparticle with concentrations is shown in FIGS. 8 and 9.

Figure 8:
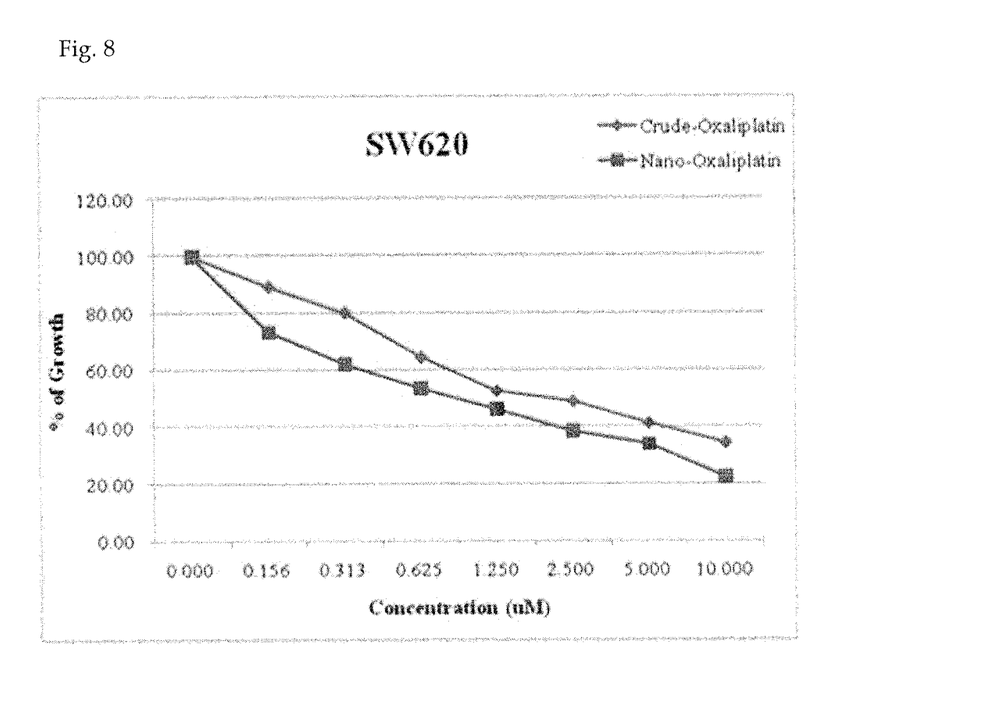
FIG. 8 shows a result of comparing $GI_{50}$ value of oxaliplatin powder and nanoparticle for SW620 cells.
Figure 9:
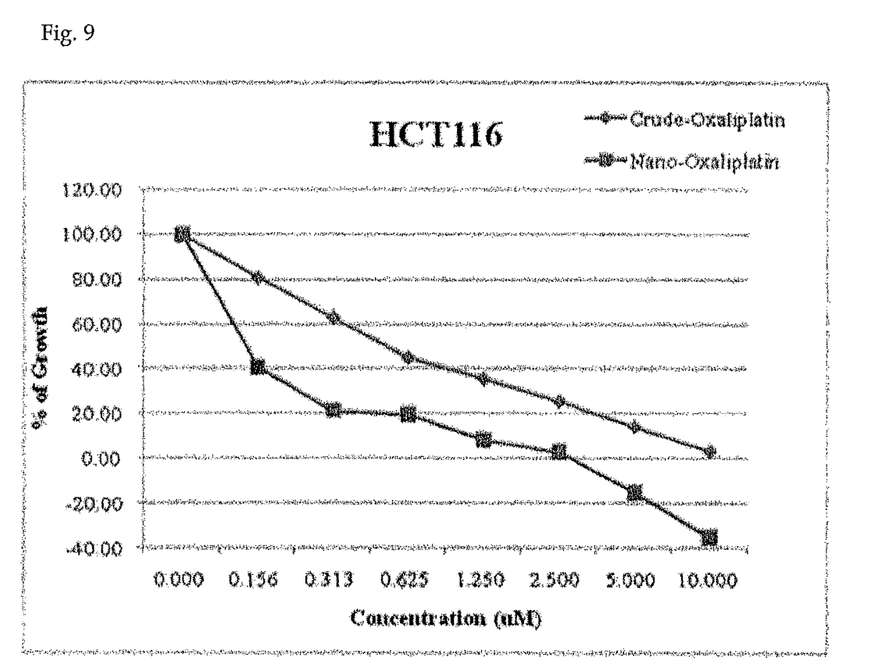
FIG. 9 shows a result of comparing $GI_{50}$ value of oxaliplatin powder and nanoparticle for HCT116 cells.

As seen from FIGS. 8 and 9, $GI_{50}$ value of the oxaliplatin powder for the SW620 and HCT116 cells was 2.22 μM and 0.55 μM, respectively, whereas that of the oxaliplatin nanoparticle was only 0.92 μM and 0.13 μM. That is to say, the oxaliplatin nanoparticle exhibited about 2.4 and 4.2 times improved anticancer activity for the colon cancer cells.

Test Example 5

Comparison of Anticancer Activity In Vivo

Human HT-29 colon cancer cells were mixed with PBS at a concentration of about $7 \times 10^7$ cells/mL and 0.1 mL was subcutaneously injected to nude mice. When the tumor area reached 5 $cm^2$, administration of the test compound was initiated.

Figure 10:
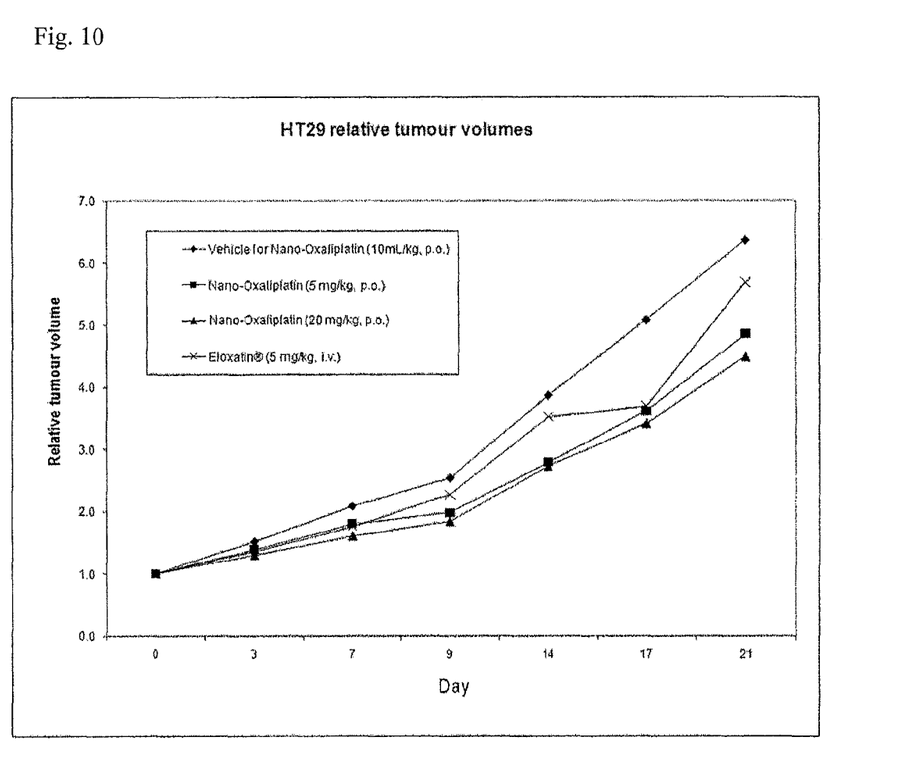
FIG. 10 shows a result of comparing relative tumor volume after orally administering the oxaliplatin nanoparticle prepared in Example 5 or injecting Eloxatin to a tumor-bearing nude mouse.

The tumor-bearing nude mice were divided into 4 groups to which 0.5% sodium carboxymethyl cellulose (10 mL/kg), the oxaliplatin nanoparticle of Example 5 (5 mg/kg or 20 mg/kg) or Eloxatin (5 mg/kg) was administered. The sodium carboxymethyl cellulose and the oxaliplatin nanoparticle were orally administered every day for 20 days, and Eloxatin was intravenously injected once a week, 3 times per each. Tumor volume was measured after 21 days and the result is given in Table 3. A result of comparing relative tumor volume with time is shown in FIG. 10. The tumor volume was calculated from $(W^2 \times L)/2$, where W is the width and L is the length of the tumor.

TABLE 3

|  | Anticancer activity (%) | Tumor volume (± S.E.M. mm³) |
|---|---|---|
| Sodium carboxymethyl cellulose | — | 839.9 ± 96.9 |
| Oxaliplatin nanoparticle (5 mg/kg, p.o.) | 36 | 568.6 ± 117.0 |
| Oxaliplatin nanoparticle (20 mg/kg, p.o.) | 43 | 513.2 ± 81.2 |
| Eloxatin ® (5 mg/kg, i.v.) | 44 | 505.7 ± 67.2 |

As seen from Table 3 and FIG. 10, it was confirmed that the oxaliplatin nanoparticle of the present invention can exhibit comparable or better anticancer effect when administered orally as compared to Eloxatin administered via injection.

Preparation Example 1

Suspension

The oxaliplatin nanoparticle of Example 5 (10 g) was sieved (35 mesh) and added to purified water (20 mL) containing sodium carboxymethyl cellulose (100 mg) to obtain a suspension.

Preparation Example 2

Tablet

The oxaliplatin nanoparticle of Example 5 (12 g) was sieved (35 mesh) and mixed with crospovidone (3 g), lactose (18.35 g) and polyvinylpyrrolidone (0.9 g). After lubricating with magnesium stearate (0.45 g) and colloidal silicon dioxide (0.3 g) for 5 minutes, the resultant was compressed into a tablet.

Preparation Example 3

Tablet

The oxaliplatin nanoparticle of Example 5 (6 g) was sieved (35 mesh) and mixed with crospovidone (3 g), lactose (24.35 g) and polyvinylpyrrolidone (0.9 g). After lubricating with magnesium stearate (0.45 g) and colloidal silicon dioxide (0.3 g) for 5 minutes, the resultant was compressed into a tablet.

Preparation Example 4

Capsule

The oxaliplatin nanoparticle of Example 5 (12 g) was sieved (35 mesh) and mixed with crospovidone (1 g). After lubricating with magnesium stearate (0.1 g), the resulting mixture was filled in a hard gelatin capsule.

Comparative Example

Tablet

Oxaliplatin powder (5 g) was sieved (35 mesh) and mixed with poloxamer (5 g), mannitol (2 g), crospovidone (3 g), lactose (18.35 g) and polyvinylpyrrolidone (0.9 g). After lubricating with magnesium stearate (0.45 g) and colloidal silicon dioxide (0.3 g) for 5 minutes, the resultant was compressed into a tablet.

Test Example 6

Measurement of Pharmacokinetic Parameters of Oxaliplatin Nanoparticle

The tablets and suspension prepared in Preparation Examples 1-3 and Comparative Example were orally administered Sprague-Dawley (SD) rats at a dosage of 10 mg/kg. Blood was taken 5, 10, 15 and 30 minutes and 1, 2, 4, 7 and 24 hours after the administration and the concentration of platinum in the blood was analyzed for measurement of pharmacokinetic parameters. Among the pharmacokinetic parameters, bioavailability was determined relative to that of the intravenously injected control substance Eloxatin (5 mg/kg) as 100.

TABLE 4

| Pharmacokinetic parameters of oxaliplatin preparations (number of animals (rats) = 6) | | | | |
|---|---|---|---|---|
|  | Comparative Example | Preparation Example 1 | Preparation Example 2 | Preparation Example 3 |
| $T_{max}$ (hr) | 0.25 | 0.25 | 0.25 | 0.3 |
| $C_{max}$ (ng/mL) | 304.6 | 8414.8 | 8621.8 | 10764.8 |
| AUC (ng · hr/mL) | 3733.9 | 65134.7 | 22280.4 | 35210.1 |
| Bioavailability (%) | 5.2 | 125.1 | 31.1 | 67.7 |

As seen from Table 4, when the oxaliplatin nanoparticle prepared in accordance with the present invention was administered as tablet or suspension, maximum serum concentration, AUC and bioavailability were significantly improved as compared to when oxaliplatin powder was intravenously injected. Accordingly, it can be seen that the nanoparticle according to the present invention can greatly increase the drug bioavailability.

What is claimed is:

1. A method for preparing an oxaliplatin nanoparticle for oral administration, comprising:
   dissolving oxaliplatin in a cosolvent which is water, dimethyl sulfoxide (DMSO) or a mixture thereof to obtain an aqueous mixture solution;
   mixing a solid lipid with a surfactant to obtain a lipid mixture solution;
   adding the lipid mixture solution to the aqueous mixture solution to obtain an emulsion and then cooling and drying the same to obtain a solid; and
   adding the solid to a reactor, pressurizing above a supercritical condition by adding a supercritical fluid gas and removing the solid lipid and the cosolvent using the supercritical fluid gas to obtain an oxaliplatin nanoparticle; and
   wherein the oxaliplatin and the surfactant are included at a weight ratio of 1:0.1-2.0.

2. The method for preparing an oxaliplatin nanoparticle for oral administration according to claim 1, wherein the solid lipid is a $C_{10}$-$C_{22}$ alcohol.

3. The method for preparing an oxaliplatin nanoparticle for oral administration according to claim 1, wherein the surfactant is selected from gelucire, solutol and poloxamer.

4. The method for preparing an oxaliplatin nanoparticle for oral administration according to claim 1, wherein said obtaining the aqueous mixture solution further comprises adding mannitol to the cosolvent as an anticoagulant.

5. The method for preparing an oxaliplatin nanoparticle for oral administration according to claim 1, wherein, when adding the lipid mixture solution to the aqueous mixture solution to obtain the emulsion, heating is conducted at 40-100° C.

6. The method for preparing an oxaliplatin nanoparticle for oral administration according to claim 1, wherein, when removing the solid lipid, the pressure inside the reactor is controlled between 50 and 200 atm and the temperature inside the reactor is controlled between 10 and 40° C.

\* \* \* \* \*